United States Patent
Yu et al.

(10) Patent No.: US 9,347,062 B2
(45) Date of Patent: May 24, 2016

(54) INTERFERING RNA DELIVERY SYSTEM AND USES THEREOF

(71) Applicant: Arrowhead Research Corporation, Pasadena, CA (US)

(72) Inventors: Ying Yu, Fort Worth, TX (US); Jon E. Chatterton, Fort Worth, TX (US)

(73) Assignee: Arrowhead Research Corporation, Pasadena, CA (US)

( * ) Notice: Subject to any disclaimer, the term of this patent is extended or adjusted under 35 U.S.C. 154(b) by 0 days.

(21) Appl. No.: 14/156,227

(22) Filed: Jan. 15, 2014

(65) Prior Publication Data

US 2014/0194359 A1    Jul. 10, 2014

Related U.S. Application Data

(66) Division of application No. 13/706,891, filed on Dec. 6, 2012, now abandoned, Substitute for application No. 61/583,772, filed on Jan. 6, 2012.

(51) Int. Cl.

| | |
|---|---|
| *A61K 38/16* | (2006.01) |
| *C07K 14/00* | (2006.01) |
| *C12N 15/11* | (2006.01) |
| *C12N 15/113* | (2010.01) |
| *A61K 47/48* | (2006.01) |
| *A61K 48/00* | (2006.01) |
| *C12N 15/87* | (2006.01) |

(52) U.S. Cl.
CPC ........ *C12N 15/113* (2013.01); *A61K 47/48246* (2013.01); *A61K 47/48315* (2013.01); *A61K 48/0025* (2013.01); *A61K 48/0033* (2013.01); *C12N 15/111* (2013.01); *C12N 15/87* (2013.01); *C12N 15/1137* (2013.01); *C12N 2310/14* (2013.01); *C12N 2310/3513* (2013.01); *C12N 2320/32* (2013.01); *C12Y 502/01008* (2013.01)

(58) Field of Classification Search
CPC .................... A61K 47/48246; A61K 48/0025; A61K 48/0033; A61K 47/48315; C12N 15/111; C12N 15/87; C12N 15/1137; C12N 2310/14; C12N 2310/3513; C12N 2320/32; C12N 15/113; C12Y 502/01008
See application file for complete search history.

(56) References Cited

U.S. PATENT DOCUMENTS

| | | |
|---|---|---|
| 2006/0166919 A1 | 7/2006 | Shepard et al. |
| 2006/0172961 A1 | 8/2006 | Clark et al. |
| 2006/0172963 A1 | 8/2006 | Shepard et al. |
| 2006/0172965 A1 | 8/2006 | Shepard et al. |
| 2006/0223773 A1 | 10/2006 | Clark et al. |
| 2007/0149473 A1 | 6/2007 | Chatterton et al. |
| 2007/0155690 A1 | 7/2007 | Chatterton et al. |
| 2009/0156470 A1 | 6/2009 | Chatterton ........................ 514/8 |
| 2010/0183558 A1 | 7/2010 | Lai et al. |
| 2010/0203611 A1 | 8/2010 | Ishizaka et al. |

FOREIGN PATENT DOCUMENTS

| | | |
|---|---|---|
| EP | 2130837 A1 | 12/2009 |
| WO | 2008108505 A1 | 9/2008 |
| WO | 20100045659 A1 | 4/2010 |
| WO | 2011066578 A1 | 6/2011 |

OTHER PUBLICATIONS

Unnamalai et al, Cationic oligopeptide-mediated delivery of dsRNA for post-transcriptional gene silencing in plant cells, FEBS Letters, 2004, 566, pp. 307-310.*

Basics and Tips of Affinity Purification, from ABRF 2009: Optimization and Application of Existing and Emerging Biotechnologies, pp. 1-32, Feb. 7-10, 2009.*

Eguchi et al.; "siRNA delivery using peptide transduction domains"; Trends in Pharmacological Sciences; vol. 30; No. 7; pp. 341-345 (Jul. 1, 1999).

Mukai et al.; "Creation of novel protein transduction domain (PTD) mutants by a phage display-based high-throughput screening system"; Biological & Pharmaceutical Bulletin; vol. 29; No. 8; pp. 1570-1574 (Aug. 2006).

Chauhan et al; "The taming of the cell penetrating domain of the HIV Tat: Myths and realities"; Journal of Controlled Release; vol. 117; No. 2; pp. 148-162 (Jan. 30, 2007).

International Search Report and Written Opinion corresponding to PCT Application Serial No. PCT/US2012/068168 dated Apr. 19, 2013.

Bullock et al.; "Permeation peptide conjugates for in-vivo molecular imaging applications"; Molecular Imaging; vol. 5; No. 1; pp. 1-15 (Jan. 2006).

Elbashir et al.; "RNA interference is mediated by 21- and 22-nucleotide RNAs"; Genes and Development; vol. 15; pp. 188-200 (2001).

Fire et al.; "Potent and specific genetic interference by double-stranded RNA in caenorhabditis elegans"; Letters to Nature; Nature; vol. 391; pp. 806-811 (Feb. 19, 2008).

Jarver and Langel; "The use of cell-penetrating peptides as a tool for gene regulation" Research Focus; Reviews; Drug Discovery Today; vol. 9; pp. 395-402 (May 9, 2004).

Kumar et al.; "Transvascular delivery of small interfering RNA to the central nervous system"; Nature; vol. 448; pp. 39-43 (2007).

Lo and Wang; "An endosomolytic tat peptide produced by incorporation of histidine and cysteine residues as a nonviral vector for DNA transfection"; Biomaterials; vol. 29; pp. 2408-2414 (2008).

(Continued)

*Primary Examiner* — Julie Ha
*Assistant Examiner* — Li Ni Komatsu

(57) ABSTRACT

The invention provides a delivery system comprising a cell penetrating peptide, 10 histidines, and an interfering RNA molecule. The system can be used for delivering interfering RNA molecules into a cell in vivo or in vitro. Therapeutic uses for the delivery system are also provided.

7 Claims, 2 Drawing Sheets

(56) References Cited

OTHER PUBLICATIONS

Meade and Dowdy; "Exogenous siRNA delivery using peptide transduction domains/cell penetrating peptides"; Advanced Drug Delivery Reviews; vol. 59; pp. 134-140 (2007).

Mukai et al.; "Creation of novel protein transduction domain (PTD) mutants by a phage display-based high-throughput screening system" Biol. Pharm. Bull.; vol. 29; No. 8; pp. 1570-1574 (2006).

Pang et al.; "Preliminary characterization of a transformed cell strain derived from human trabecular meshwork"; Current Eye Research; vol. 13; No. 1; pp. 51-63 (1994).

Wadia et al; "Transducible TAT-HA fusogenic peptide enhances escape of TAT-fusion proteins after lipid raft macropinocytosis"; Technical Reports; Nature Medicine; vol. 10; No. 3; pp. 310-315 (Mar. 2004).

Wadia and Dowdy; "Modulation of cellular function by TAT mediated transduction of full length proteins"; Current Protein and Peptide Science; vol. 4; pp. 97-104 (2003).

* cited by examiner

INTERFERING RNA DELIVERY SYSTEM AND USES THEREOF

CROSS-REFERENCE TO RELATED APPLICATION

The present application is a divisional of U.S. application Ser. No. 13/706,891 filed Dec. 6, 2012 (pending), which claims priority to U.S. Provisional Patent Application No. 61/583,772 filed Jan. 6, 2012, the entire contents of which are incorporated herein by reference.

FIELD OF THE INVENTION

The invention relates to a delivery system for delivering interfering RNA molecules into a cell and methods for using the delivery system. The delivery system comprises a YM3-10H peptide. The invention also relates to methods of delivering interfering RNA to a patient in need thereof.

BACKGROUND OF THE INVENTION

RNA interference (RNAi) is a process by which double-stranded RNA (dsRNA) is used to silence gene expression. RNAi is induced by short (i.e. <30 nucleotide) double stranded RNA ("dsRNA") molecules which are present in the cell (Fire et al., 1998, Nature 391:806-811). These short dsRNA molecules called "short interfering RNA" or "siRNA," cause the destruction of messenger RNAs ("mRNAs") which share sequence homology with the siRNA (Elbashir et al., 2001, Genes Dev, 15:188-200). It is believed that one strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

RNAi provides a very exciting approach to treating and/or preventing diseases. Some major benefits of RNAi compared with various traditional therapeutic approaches include: the ability of RNAi to target a very particular gene involved in the disease process with high specificity, thereby reducing or eliminating off target effects; RNAi is a normal cellular process leading to a highly specific RNA degradation; and RNAi does not trigger a host immune response as in many antibody based therapies.

Several interfering RNA delivery methods are being tested/developed for in vivo use. For example, siRNAs can be delivered "naked" in saline solution; complexed with polycations, cationic lipids/lipid transfection reagents, or cationic peptides; as components of defined molecular conjugates (e.g., cholesterol-modified siRNA, TAT-DRBD/siRNA complexes); as components of liposomes; and as components of nanoparticles. These approaches have shown varying degrees of success. Thus, there remains a need for new and improved methods for delivering siRNA molecules in vivo to achieve and enhance the therapeutic potential of RNAi.

Several cell-penetrating peptides (CPPs) or membrane permeant peptides (MPPs) have been described (Jarver and Langel, 2004, Drug Discov Today 9:395-402) as conjugates to deliver peptides into cells. Of these, the protein transduction domain (PTD) of the HIV-1 TAT protein appears to be particularly effective. The TAT peptide has been used to deliver biologically active cargo to cells in vitro and in vivo (Wadia et al., 2003, Curr Protein Pept Sci. 4:97-104; Bullok K E et al., 2006, Mol Imaging 5:1-15). Dowdy's group also demonstrated that co-delivery of the HA2 peptide enhances release of cargo from macropinosomes following TAT-mediated delivery (Wadia et al., 2004, Nat Med. 10:310-315).

Several groups have explored the use of CPPs to deliver siRNA (reviewed in Meade and Dowdy, 2007, Adv Drug Deliv Rev. 59:134-140). This review points out the problems associated with direct attachment of siRNA to TAT. The protein transduction domain (PTD) of the HIV-1 TAT protein is a CPP that appears to be particularly effective. The TAT peptide has been used to deliver biologically active cargo to cells in vitro and in vivo (Wadia and Dowdy, 2003, Curr Protein Pept Sci. 4:97-104; Bullok et al., 2006, Mol Imaging 5:1-15). The addition of 10 histidine residues (10H) to TAT has been shown to facilitate endosomal release of DNA (Lo & Wang, Biomaterials 29:2408-2414, 2008).

While several groups have explored the use of CPPs to deliver interfering RNA molecules (See Meade and Dowdy, 2007, Adv Drug Deliv Rev. 59:134-140), the main challenge to this approach involves linking the interfering RNA to the CPPs while maintaining the ability of the complex to interact with and enter the intracellular environment. In particular, the negative charge of the interfering RNA neutralizes the positively charged CPPs, which renders such complexes incapable of cellular delivery. Thus, there remains a need to identify effective means for delivering interfering RNA molecules to target cells.

SUMMARY OF THE INVENTION

The invention provides an interfering RNA delivery system comprising an interfering RNA molecule attached to a YM3-10H peptide. The invention also provides a method for delivering an interfering RNA molecule into a cell, in vitro or in vivo, comprising: attaching an interfering RNA molecule to a YM3-10H peptide, thereby forming an interfering RNA delivery system; and administering the system to the cell under conditions suitable for the system to enter the cell.

In one aspect, an interfering RNA molecule in a delivery system of the invention can attenuate expression of a target mRNA in a target cell. Thus, the invention provides methods for attenuating expression of a target mRNA in a cell comprising administering a delivery system of the invention to the cell.

The invention further provides pharmaceutical compositions comprising an interfering RNA delivery system of the invention. The pharmaceutical compositions can be used in therapeutic applications to treat various disorders or diseases in which inhibition of a target gene is desired.

In addition, the invention provides methods of treating or preventing an ocular disorder in a patient, comprising administering to the patient an interfering RNA delivery system as described herein to the patient, wherein the interfering RNA molecule can attenuate expression of a gene associated with the ocular disorder. In certain aspects, the ocular disorder is associated with ocular angiogenesis, dry eye, ocular inflammatory conditions, ocular hypertension, or glaucoma. In other aspects, the conjugate is administered by intraocular injection, ocular topical application, subconjunctival injection, intravitreal injection, anterior or posterior juxtascleral injection, intravenous injection, oral administration, intramuscular injection, intraperitoneal injection, transdermal application, intranasal application, or transmucosal application.

Specific preferred embodiments of the invention will become evident from the following more detailed description of certain preferred embodiments and the claims.

DETAILED DESCRIPTION OF THE INVENTION

Figure 1:
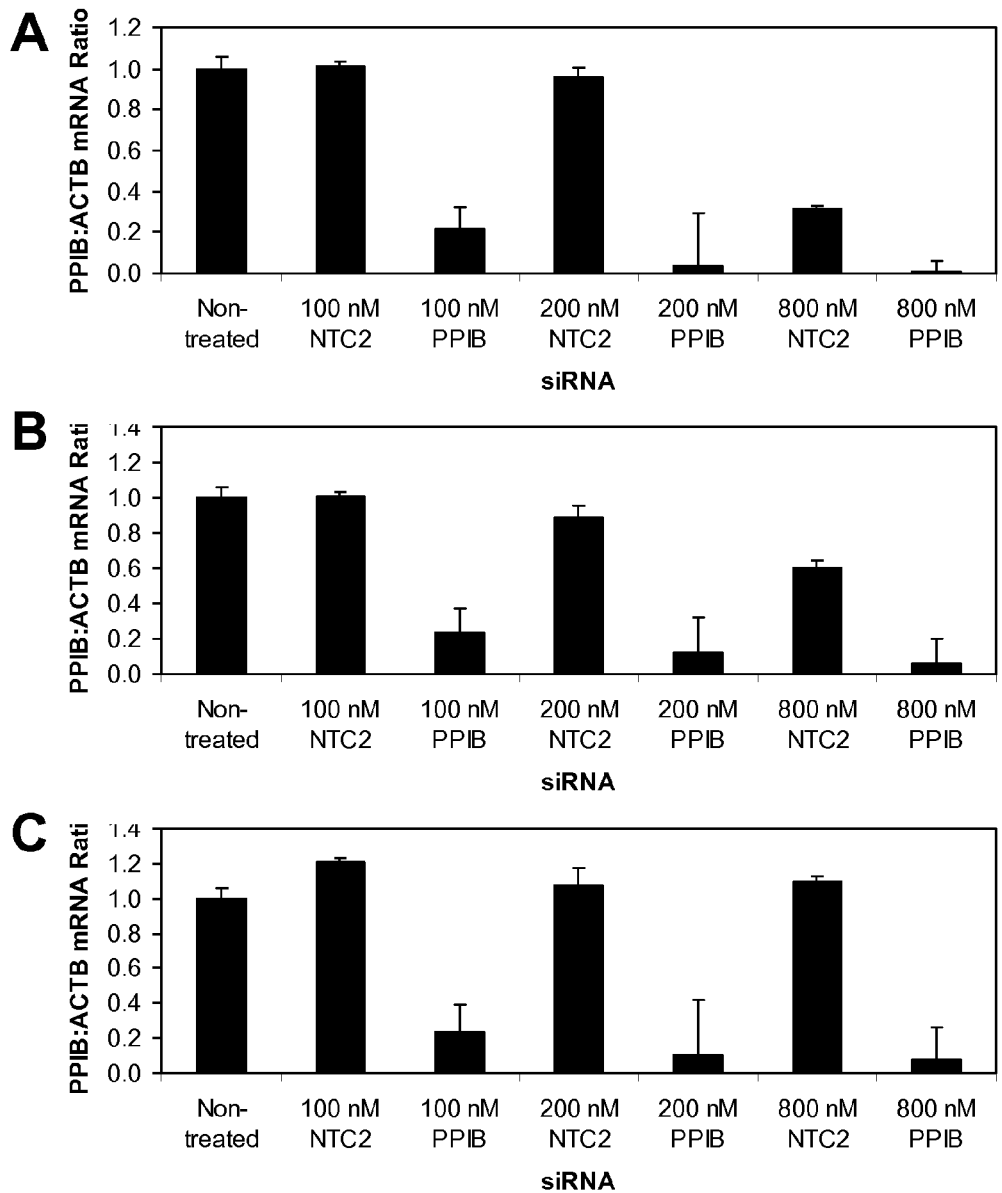
FIG. 1A shows a graph demonstrating in vitro siRNA delivery to NRK52E cells using TAT-10H peptides at various concentrations.
FIG. 1B shows a graph demonstrating in vitro siRNA delivery to NRK52E cells using CTP-10H peptides at various concentrations.
FIG. 1C shows a graph demonstrating in vitro siRNA delivery to NRK52E cells using YM3-10H peptides at various concentrations.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides an interfering RNA delivery system comprising an interfering RNA molecule linked to a YM3-10H peptide. In a particular embodiment, the YM3-10H peptide is attached covalently or non-covalently to the 3' end of a sense strand of an interfering RNA molecule.

In one embodiment, the YM3-10H peptide is mixed with siRNA at a peptide molar excess (for example, 20:1, 10:1, 5:1, or 2:1 peptide:interfering RNA ratio). In this case, the cationic YM3 sequence facilitates the connection between the YM3-10H peptide and the interfering RNA molecule, neutralizes the interfering RNA molecule negative charge, and facilitates uptake by cells.

YM3 is a protein transduction domain consisting of the amino acid sequence THRLPRRRRRR (SEQ ID NO: 1) as described in Mukai et al., *Biol. Pharm. Bull.* 29:1570-1574, 2006.

YM3-10H is a peptide that comprises YM3 and 10 histidine residues. In one embodiment, YM3-10H has an amino acid sequence of CHHHHHTHRLPRRRRRRHHHHHC (SEQ ID NO: 2), in which a terminal cysteine residue to each end of 5 histidine stretches on either end of the YM3 peptide.

In another embodiment, a YM3-10H peptide is covalently attached to an interfering RNA molecule, such as a siRNA, with or without a terminal cysteine residue at the end connected to the interfering RNA molecule. For example:

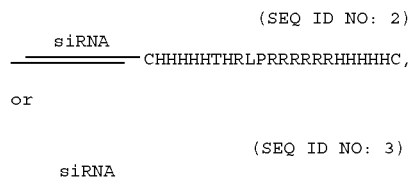

(SEQ ID NO: 2)
siRNA————CHHHHHTHRLPRRRRRRHHHHHC, or (SEQ ID NO: 3)
siRNA————HHHHHTHRLPRRRRRRHHHHHC.

In other embodiments, histidine residues in a YM3-10H peptide can be all at one end of the peptide sequence. For example:

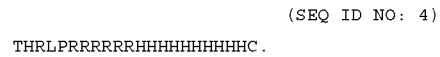

(SEQ ID NO: 4)
THRLPRRRRRRHHHHHHHHHHC.

In other embodiments, spacer peptides, (such as diglycine), can also be inserted between the interfering RNA molecule and the spacer, between the YM3 sequence and histidine residues, interrupting the polyhistidine sequence, or all three orientations. For example:

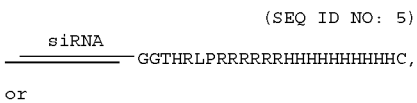

(SEQ ID NO: 5)
siRNA————GGTHRLPRRRRRRHHHHHHHHHHC, or (SEQ ID NO: 6)
siRNA————THRLPRRRRRRGGHHHHHHHHHC, or (SEQ ID NO: 7)
siRNA————THRLPRRRRRRHHHHHGGHHHHHC.

Concatemers of YM3-10H peptide sequences are also envisioned to optimize the peptide:interfering RNA ratio. The concatemerization can be accomplished, for instance, via formation of disulfide bonds between the terminal cysteine residues or through the use of alternative chemistries. For example:

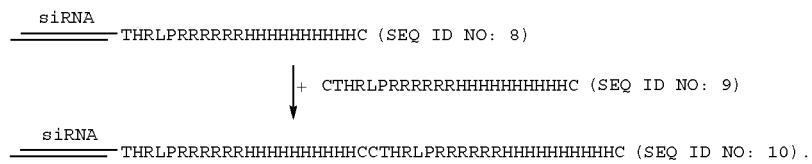

Such concatemers may contain more than one of the same YM3-10H peptide, or a combination of various YM3-10H peptides as provided herein or otherwise derived from the present disclosure.

In certain embodiments, the amino acids in a YM3-10H peptide can be all L-isomers, all D-isomers, or a mixture of L- and D-isomers. In other embodiments, the order of the amino acids set forth in a YM3-10H peptide can be reversed, again with all possible combinations of L- and D-isomers. In addition, terminal amino acid residues other than cysteine can also be used in YM3-10H peptides, for example, alanine or serine instead of cysteine.

As used herein, the phrase "interfering RNA delivery system" refers to a system that comprises a YM3-10H peptide and an interfering RNA molecule, which is capable of delivering the interfering RNA molecule into a cell. In certain embodiments, the interfering RNA delivery system can be administered to a subject in need thereof.

In certain embodiments, an interfering RNA delivery system as described herein can be used in a method of delivering an interfering RNA molecule into a cell. The cell can be an isolated cell (e.g. in cell culture) or associated with a subject in which inhibiting expression of a target gene is desired. The cell may also be used in a ex vivo therapeutic method, in which the cell is taken from a subject and reintroduced into the same or a different subject after the interfering RNA delivery system has been introduced into the cell.

As used herein, the term "subject" or "patient" refers to human and non-human animals. The term "non-human animals" refers to vertebrates and non-vertebrates, including but, not limited to, primates, rabbits, pigs, horses, dogs, cats, sheep, and cows. In one embodiment, a patient has an ocular disorder or is at risk of having an ocular disorder. Ocular structures associated with such disorders may include the eye, retina, choroid, lens, cornea, trabecular meshwork, iris, optic nerve, optic nerve head, sclera, anterior or posterior segment, or ciliary body, for example. In certain embodiments, a patient has an ocular disorder associated with trabecular meshwork (TM) cells, ciliary epithelium cells, or another cell type of the eye.

The term "ocular disorder" as used herein includes conditions associated with ocular angiogenesis, dry eye, inflammatory conditions, ocular hypertension and ocular diseases associated with elevated intraocular pressure (IOP), such as glaucoma.

The term "ocular angiogenesis," as used herein, includes ocular pre-angiogenic conditions and ocular angiogenic conditions, and includes ocular angiogenesis, ocular neovascularization, retinal edema, diabetic retinopathy, sequela associated with retinal ischemia, posterior segment neovascularization (PSNV), and neovascular glaucoma, for example. The interfering RNAs used in a method of the invention are useful for treating patients with ocular angiogenesis, ocular neovasularization, retinal edema, diabetic retinopathy, sequela associated with retinal ischemia, posterior segment neovascularization (PSNV), and neovascular glaucoma, or patients at risk of developing such conditions, for example.

The term "ocular neovascularization" includes age-related macular degeneration, cataract, acute ischemic optic neuropathy (AION), commotio retinae, retinal detachment, retinal tears or holes, iatrogenic retinopathy and other ischemic retinopathies or optic neuropathies, myopia, retinitis pigmentosa, and/or the like.

The term "inflammatory condition," as used herein, includes conditions such as ocular inflammation and allergic conjunctivitis.

The interfering RNA delivery system of the invention is useful for attenuating expression of particular genes in a patient (i.e. subject) using RNA interference.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. siRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

In certain embodiments, the invention provides methods of delivering interfering RNA to inhibit the expression of a target mRNA thus decreasing target mRNA levels in patients with target mRNA-related disorders.

The phrase "attenuating expression" with reference to a gene or an mRNA as used herein means administering or expressing an amount of interfering RNA (e.g., an siRNA) to reduce translation of a target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Attenuating expression of a target gene by an interfering RNA molecule of the invention can be inferred in a human or other mammal by observing an improvement in symptoms of the disorder.

In one embodiment, a single interfering RNA is delivered to decrease target mRNA levels.

In other embodiments, two or more interfering RNAs targeting the mRNA are administered to decrease target mRNA levels. The interfering RNAs may be delivered through linkage to the same YM3-10H peptide or through linkage to separate YM3-10H peptide(s) (e.g. each interfering RNA can be pre-mixed and added to YM3-10H peptide or each interfering RNA can be independently mixed with YM3-10H peptide, followed by combining the individual interfering RNA/YM3-10H peptide complexes).

As used herein, the terms "interfering RNA" and "interfering RNA molecule" refer to all RNA or RNA-like molecules that can interact with RISC and participate in RISC-mediated changes in gene expression. Examples of other interfering RNA molecules that can interact with RISC include short hairpin RNAs (shRNAs), single-stranded siRNAs, microRNAs (miRNAs), picoRNAs (piRNAs), and dicer-substrate 27-mer duplexes. Examples of "RNA-like" molecules that can interact with RISC include siRNA, single-stranded siRNA, miRNA, piRNA, asymmetrical siRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, piRNA, asymmetrical siRNA, and dicer-substrate 27-mer duplexes are subsets of "interfering RNAs" or "interfering RNA molecules."

The term "siRNA" as used herein refers to a double-stranded interfering RNA unless otherwise noted. Typically, an siRNA used in a method of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). Typically, an interfering RNA used in a method of the invention has a length of about 19 to 49 nucleotides. The phrase "length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

The interfering RNA used in a delivery system and method of the invention can be unmodified or can be chemically stabilized to prevent degradation in the lysosome or other compartments in the endocytic pathway.

Single-stranded interfering RNA has been found to effect mRNA silencing, albeit less efficiently than double-stranded RNA. Therefore, embodiments of the present invention also provide for administration of a single-stranded interfering RNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, to reduce off-target effects, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a biotin molecule, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, to reduce off-target effects, or to direct localization or targeting.

In certain embodiments, an interfering molecule of the invention comprises at least one of the modifications as described above.

The phrases "target sequence" and "target mRNA" as used herein refer to the mRNA or the portion of the mRNA sequence that can be recognized by an interfering RNA used in a method of the invention, whereby the interfering RNA can silence gene expression as discussed herein. Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, or Genscript web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Interfering RNA target sequences (e.g., siRNA target sequences) within a target mRNA sequence are selected using available design tools as discussed above. Interfering RNAs corresponding to a target sequence are then tested in vitro by transfection of cells expressing the target mRNA followed by assessment of knockdown as described herein. The interfering RNAs can be further evaluated in vivo using animal models as described herein.

The ability of interfering RNA to knock-down the levels of endogenous target gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression. Human corneal epithelial cells or other human ocular cell lines may also be use for an evaluation of the ability of interfering RNA to knock-down levels of an endogenous target gene.

In certain embodiments, an interfering RNA delivery system comprises an interfering RNA molecule that targets a gene associated with an ocular disorder. Examples of mRNA target genes for which interfering RNAs of the present invention are designed to target include genes associated with the disorders that affect the retina, genes associated with glaucoma, and genes associated with ocular inflammation.

Examples of mRNA target genes associated with the retinal disorders include TEK tyrosine kinase, endothelial (TEK); complement factor B (CFB); hypoxia-inducible factor 1, α subunit (HIF1A); HtrA serine peptidase 1 (HTRA1); platelet-derived growth factor receptor β (PDGFRB); chemokine, CXC motif, receptor 4 (CXCR4); insulin-like growth factor I receptor (IGF1R); angiopoietin 2 (ANGPT2); v-fos FBJ murine osteosarcoma viral oncogene homolog (FOS); cathepsin L1, transcript variant 1 (CTSL1); cathepsin L1, transcript variant 2 (CTSL2); intracellular adhesion molecule 1 (ICAM1); insulin-like growth factor I (IGF1); integrin α5 (ITGA5); integrin β1 (ITGB1); nuclear factor kappa-B, subunit 1 (NFKB1); nuclear factor kappa-B, subunit 2 (NFKB2); chemokine, CXC motif, ligand 12 (CXCL12); tumor necrosis factor receptor 1 (TNFR1); vascular endothelial growth factor (VEGF); vascular endothelial growth factor receptor 1 (VEGFR1); tumor necrosis factor-alpha-converting enzyme (TACE); and kinase insert domain receptor (KDR).

Examples of target genes associated with glaucoma include carbonic anhydrase II (CA2); carbonic anhydrase IV (CA4); carbonic anhydrase XII (CA12); β1 andrenergic receptor (ADBR1); β2 andrenergic receptor (ADBR2); acetylcholinesterase (ACHE); Na+/K+-ATPase; solute carrier family 12 (sodium/potassium/chloride transporters), member 1 (SLC12A1); solute carrier family 12 (sodium/potassium/chloride transporters), member 2 (SLC12A2); connective tissue growth factor (CTGF); serum amyloid A (SAA); secreted frizzled-related protein 1 (sFRP1); gremlin (GREM1); lysyl oxidase (LOX); c-Maf; rho-associated coiled-coil-containing protein kinase 1 (ROCK1); rho-associated coiled-coil-containing protein kinase 2 (ROCK2); plasminogen activator inhibitor 1 (PAI-1); endothelial differentiation, sphingolipid G-protein-coupled receptor, 3 (Edg3 R); myocilin (MYOC); NADPH oxidase 4 (NOX4); Protein Kinase Cδ (PKCδ); Aquaporin 1 (AQP1); Aquaporin 4 (AQP4); members of the complement cascade; ATPase, H+ transporting, lysosomal V1 subunit A (ATP6V1A); gap junction protein α-1 (GJA1); formyl peptide receptor 1 (FPR1); formyl peptide receptor-like 1 (FPRL1); interleukin 8 (IL8); nuclear factor kappa-B, subunit 1 (NFKB1); nuclear factor kappa-B, subunit 2 (NFKB2); presenilin 1 (PSEN1); tumor necrosis factor-alpha-converting enzyme (TACE); transforming growth factor β2 (TGFB2); transient receptor potential cation channel, subfamily V, member 1 (TRPV1); chloride channel 3 (CLCN3); gap junction protein α5 (GJA5); tumor necrosis factor receptor 1 (TNFR1); and chitinase 3-like 2 (CHI3L2).

Examples of mRNA target genes associated with ocular inflammation include tumor necrosis factor receptor superfamily, member 1A (TNFRSF1A); phosphodiesterase 4D, cAMP-specific (PDE4D); histamine receptor H1 (HRH1); spleen tyrosine kinase (SYK); interkeukin 1β (IL1B); nuclear factor kappa-B, subunit 1 (NFKB1); nuclear factor kappa-B, subunit 2 (NFKB2); and tumor necrosis factor-alpha-converting enzyme (TACE).

Such target genes are described, for example, in U.S. Patent Applications having Publication Nos. 20060166919, 20060172961, 20060172963, 20060172965, 20060223773, 20070149473, and 20070155690, the disclosures of which are incorporated by reference in their entirety.

In certain embodiments, the invention provides a pharmaceutical composition comprising an interfering RNA delivery system of the invention. In certain embodiments, the composition is in a pharmaceutically acceptable carrier in a therapeutically effective amount.

Pharmaceutical compositions are formulations that comprise interfering RNAs, or salts thereof, of the invention up to 99% by weight mixed with a physiologically acceptable carrier medium, including those described infra, and such as water, buffer, saline, glycine, hyaluronic acid, mannitol, and the like.

Compositions of the present invention are administered as solutions, suspensions, or emulsions. The following are examples of pharmaceutical composition formulations that may be used in the methods of the invention.

| | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

| | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

| | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

| | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

As used herein, the term "therapeutically effective amount" refers to the amount of interfering RNA or a pharmaceutical composition comprising an interfering RNA determined to produce a therapeutic response in a mammal. Such therapeutically effective amounts are readily ascertained by one of ordinary skill in the art and using methods as described herein.

Generally, a therapeutically effective amount of the interfering RNAs used in a composition of the invention results in an extracellular concentration at the surface of the target cell of from 100 pM to 25 µM, or from 1 nM to 5 µM, or from 5 nM to about 1 µM, or to about 500 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions can be delivered to the surface of the target organ one to four times per day, or on an extended delivery schedule such as daily, weekly, bi-weekly, monthly, or longer, according to the routine discretion of a skilled clinician. The pH of the formulation is about pH 4.0 to about pH 9.0, or about pH 6.0 to about pH 7.4.

A therapeutically effective amount of a formulation may depend on factors such as the age, race, and sex of the subject, the severity of the disorder, the rate of target gene transcript/protein turnover, the interfering RNA potency, and the interfering RNA stability, for example. In one embodiment, the interfering RNA is delivered topically to a target organ and reaches the target mRNA-containing tissue at a therapeutic dose thereby ameliorating target gene-associated disease process.

Therapeutic treatment of patients with interfering RNAs directed against target mRNAs is expected to be beneficial over small molecule treatments by increasing the duration of action, thereby allowing less frequent dosing and greater patient compliance, and by increasing target specificity, thereby reducing side effects.

A "pharmaceutically acceptable carrier" as used herein refers to those carriers that cause at most, little to no irritation, provide suitable preservation if needed, and deliver one or more interfering RNAs of the present invention in a homogenous dosage.

The delivery systems and compositions of the present invention may be delivered in solution, in suspension, or in bioerodible or non-bioerodible delivery devices.

The delivery systems and compositions of the present invention may be delivered via absorption, adsorption, aerosol, buccal, dermal, inhaling, intracentricular, intracranial, intradermal, intramuscular, intranasal, intraocular, intrapulmonary, intravenous, intraperitoneal, intrasternal, intrathecal, intraventricular, nasal, ocular, oral, otic, parenteral, patch, rectal, systemic, subcutaneous, sublingual, topical, or transdermal, or vaginal administration, for example.

Interfering RNA delivery systems may be delivered directly to the eye by ocular tissue injection such as periocular, conjunctival, subtenon, intracameral, intravitreal, intraocular, anterior or posterior juxtascleral, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ocular administration, the compositions of the invention can be delivered by intravitreal injection every 2-6 weeks, for example, or via topical ocular, anterior or posterior juxtascleral depot, subconjunctival, periocular, retrobulbar, subtenon, intracameral, intraocular, subretinal, or suprachoroidal administration.

For pharmaceutical delivery, compositions of the present invention may be combined with pharmaceutically acceptable preservatives, co-solvents, surfactants, viscosity enhancers, penetration enhancers, buffers, sodium chloride, or water to form an aqueous, sterile suspension or solution. Solution formulations may be prepared by dissolving the conjugate in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ointment formulation, the composition is combined with a preservative in an appropriate vehicle, such as mineral oil, liquid lanolin, or white petrolatum. Sterile gel formulations may be prepared by suspending the composition of the invention in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.).

In certain embodiments, the invention also provides a kit that includes reagents for attenuating the expression of an mRNA as cited herein in a cell. The kit contains an interfering RNA molecule conjugated to YM3-10H peptide and/or the necessary components for production of an interfering RNA molecule conjugated to a YM3-10H peptide (e.g., an interfering RNA molecule as well as the peptide and necessary materials for linking). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and a peptide. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

EXAMPLES

The following example, including the experiments conducted and results achieved is provided for illustrative purposes only and are not to be construed as limiting the invention.

Example 1

YM3-10H Peptide-Mediated siRNA Delivery

The ability of 10 histidine residues (10H) to enhance endosomal release of siRNAs delivered using certain cell penetrating peptides (CPPs) was examined. Three siRNA-delivery peptides comprising a protein transduction domain (PTD) and 10 histidines were generated: YM3-10H, CHHH-HHTHRLPRRRRRRHHHHHC (SEQ ID NO: 2); CTP-10H, CHHHHHGGRRARRRRRRHHHHHC (SEQ ID NO: 11); and TAT-10HC, CHHHHHTHYGRKKRRQRRRHHHHHC (SEQ ID NO: 12). Peptidyl-prolyl cis-trans isomerase B (PPIB) siRNA and Non-Targeting siRNA #2 (NTC2) (Thermo Fisher Scientific, Dharmacon Products, Lafayette, Colo.) were complexed with TAT-10H, CTP-10H, and YM3-10H peptides (Abgent, Inc., San Diego, Calif.) at a 20:1 peptide:siRNA molar ratio for 30 minutes at room temperature, and applied to GTM-3 cells (Pang, I. H., et al., 1994 *Curr Eye Res.* 13:51-63) at a final siRNA concentration of 100-800 nM for 1 hour. PPIB mRNA and β-actin mRNA levels were determined by Taqman qRT-PCR assay (Applied Biosystems, Austin, Tex.) at 48 hour post-transfection (FIG. 1). Data were normalized to β-actin mRNA, and expressed relative to PPIB mRNA level in non-treated cells. Delivery of PPIB siRNA using the TAT-10H (FIG. 1A), CTP-10H (FIG. 1B), and YM3-10H (FIG. 1C) peptides suppressed PPIB mRNA expression by ~80% at 100 nM siRNA and by ≥90% at 200 and 800 nM siRNA. Delivery of the NTC2 control peptide with the TAT-10H and CTP-10H peptides also resulted in significant silencing of PPIB mRNA expression at 800 nM siRNA (FIG. 1A, 1B), possibly due to a cytotoxic effect. In contrast, non-specific reduction in PPIB mRNA expression was not observed with the NTC2 siRNA delivered using the YM3-10H peptide (FIG. 1C).

Figure 2:
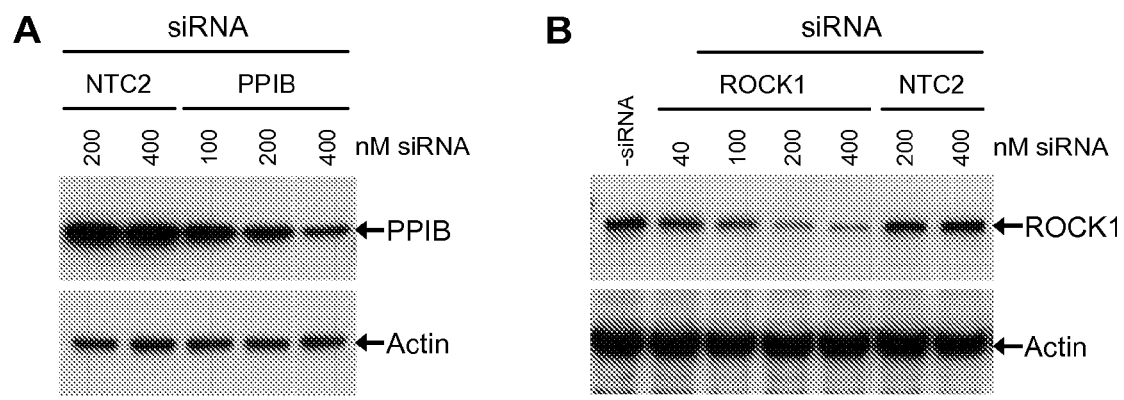
FIG. 2A shows a Western blot analysis demonstrating expression levels of NTC2 and PPIB proteins after in vitro siRNA delivery to NRK52E cells using YM3-10H peptide.
FIG. 2B shows a Western blot analysis demonstrating expression levels of NTC2 and ROCK1 proteins after in vitro siRNA delivery to NRK52E cells using YM3-10H peptide.

In addition, PPIB, ROCK1, and NTC2 siRNAs (Dharmacon) were complexed with YM3-10H peptide (Abgent) at a 20:1 peptide:siRNA molar ratio for 30 minutes at room temperature, and applied to NRK52E cells (ATCC, Manassas, Va.) at final siRNA concentrations of 40-400 nM for 1 hour. PPIB (FIG. 2A) and ROCK1 (FIG. 2B) protein expression was analyzed by western blot at 72 hour post-transfection. As shown in FIG. 2, YM3-10H-mediated transduction of NRK52E cells with PPIB and ROCK1 siRNAs at 200-400 nM caused a significant reduction in PPIB (FIG. 2A) and ROCK1 (FIG. 2B) protein expression, respectively. Transduction of the cells with the NTC2 siRNA had no effect on PPIB or ROCK1 expression. Arrows in the Figures indicate the positions of the PPIB, ROCK1, and actin bands.

These results demonstrated that linkage of siRNAs to YM3-10H peptide facilitated siRNA delivery to cultured cells.

It should be understood that the foregoing disclosure emphasizes certain specific embodiments of the invention and that all modifications or alternatives equivalent thereto are within the spirit and scope of the invention as set forth in the appended claims.

What is claimed is:

1. An interfering RNA delivery system comprising a molecular group consisting of an interfering RNA molecule linked to a YM3-10H peptide, wherein the YM3-10H peptide comprises an amino acid sequence selected from the group consisting of:

CHHHHHTHRLPRRRRRRHHHHHC and  (SEQ ID NO: 2)

HHHHHTHRLPRRRRRRHHHHHC.  (SEQ ID NO: 3)

2. The delivery system of claim 1, wherein the interfering RNA molecule is linked to the YM3-10H peptide via a covalent bond.

3. The delivery system of claim 1, wherein the interfering RNA molecule is a short interfering RNA (siRNA), micro RNA (miRNA), or short hairpin RNA (shRNA).

4. A pharmaceutical composition comprising the delivery system of claim 1 and a pharmaceutically acceptable carrier.

5. A method of delivering an interfering RNA molecule into a cell, comprising:
(a) attaching an interfering RNA molecule to a YM3-10H peptide, wherein the YM3-10H peptide comprises an amino acid sequence selected from the group consisting of:

CHHHHHTHRLPRRRRRRHHHHHC  (SEQ ID NO: 2)
and

HHHHHTHRLPRRRRRRHHHHHC,  (SEQ ID NO: 3)

thereby forming an interfering RNA delivery system; and
(b) administering the interfering RNA delivery system to the cell.

6. The method of claim 5, wherein the interfering RNA molecule is linked to the YM3-10H peptide via a covalent bond.

7. The method of claim 5, wherein the interfering RNA molecule is a siRNA, miRNA, or shRNA.

* * * * *

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: synthetic peptide

<400> SEQUENCE: 1

Thr His Arg Leu Pro Arg Arg Arg Arg Arg Arg
1               5                   10

<210> SEQ ID NO 2
<211> LENGTH: 23
<212> TYPE: PRT
<213> ORGANISM: Artificial Sequence
<220> FEATURE:
<223> OTHER INFORMATION: synthetic peptide

<400> SEQUENCE: 2

Cys His His His His His Thr His Arg Leu Pro Arg Arg Arg Arg Arg
1               5                   10                  15

Arg His His His His His Cys
            20

<210> SEQ ID NO 3
<211> LENGTH: 22
<212> TYPE: PRT
<213> ORGANISM: Artificial Sequence
<220> FEATURE:
<223> OTHER INFORMATION: synthetic peptide

<400> SEQUENCE: 3

His His His His His Thr His Arg Leu Pro Arg Arg Arg Arg Arg Arg
1               5                   10                  15

His His His His His Cys
            20

<210> SEQ ID NO 4
<211> LENGTH: 22
<212> TYPE: PRT
<213> ORGANISM: Artificial Sequence
<220> FEATURE:
<223> OTHER INFORMATION: synthetic peptide

<400> SEQUENCE: 4

Thr His Arg Leu Pro Arg Arg Arg Arg Arg Arg His His His His His
1               5                   10                  15

His His His His His Cys
            20

<210> SEQ ID NO 5
<211> LENGTH: 24
<212> TYPE: PRT
<213> ORGANISM: Artificial Sequence
```

<220> FEATURE:
<223> OTHER INFORMATION: synthetic peptide

<400> SEQUENCE: 5

Gly Gly Thr His Arg Leu Pro Arg Arg Arg Arg Arg His His His
1               5                   10                  15

His His His His His His Cys
            20

<210> SEQ ID NO 6
<211> LENGTH: 24
<212> TYPE: PRT
<213> ORGANISM: Artificial Sequence
<220> FEATURE:
<223> OTHER INFORMATION: synthetic peptide

<400> SEQUENCE: 6

Thr His Arg Leu Pro Arg Arg Arg Arg Arg Gly Gly His His His
1               5                   10                  15

His His His His His His His Cys
            20

<210> SEQ ID NO 7
<211> LENGTH: 24
<212> TYPE: PRT
<213> ORGANISM: Artificial Sequence
<220> FEATURE:
<223> OTHER INFORMATION: synthetic peptide

<400> SEQUENCE: 7

Thr His Arg Leu Pro Arg Arg Arg Arg Arg His His His His His
1               5                   10                  15

Gly Gly His His His His His Cys
            20

<210> SEQ ID NO 8
<211> LENGTH: 22
<212> TYPE: PRT
<213> ORGANISM: Artificial Sequence
<220> FEATURE:
<223> OTHER INFORMATION: synthetic peptide

<400> SEQUENCE: 8

Thr His Arg Leu Pro Arg Arg Arg Arg Arg His His His His His
1               5                   10                  15

His His His His His Cys
            20

<210> SEQ ID NO 9
<211> LENGTH: 23
<212> TYPE: PRT
<213> ORGANISM: Artificial Sequence
<220> FEATURE:
<223> OTHER INFORMATION: synthetic peptide

<400> SEQUENCE: 9

Cys Thr His Arg Leu Pro Arg Arg Arg Arg Arg His His His His
1               5                   10                  15

His His His His His His Cys
            20

<210> SEQ ID NO 10
<211> LENGTH: 45
<212> TYPE: PRT

```
<213> ORGANISM: Artificial Sequence
<220> FEATURE:
<223> OTHER INFORMATION: synthetic peptide

<400> SEQUENCE: 10

Thr His Arg Leu Pro Arg Arg Arg Arg Arg His His His His
1               5                   10                  15

His His His His His Cys Cys Thr His Arg Leu Pro Arg Arg Arg Arg
                20              25                  30

Arg Arg His His His His His His His His Cys
            35              40                  45

<210> SEQ ID NO 11
<211> LENGTH: 23
<212> TYPE: PRT
<213> ORGANISM: Artificial Sequence
<220> FEATURE:
<223> OTHER INFORMATION: synthetic peptide

<400> SEQUENCE: 11

Cys His His His His His Gly Gly Arg Arg Ala Arg Arg Arg Arg
1               5                   10                  15

Arg His His His His His Cys
            20

<210> SEQ ID NO 12
<211> LENGTH: 25
<212> TYPE: PRT
<213> ORGANISM: Artificial Sequence
<220> FEATURE:
<223> OTHER INFORMATION: synthetic peptide

<400> SEQUENCE: 12

Cys His His His His His Thr His Tyr Gly Arg Lys Lys Arg Arg Gln
1               5                   10                  15

Arg Arg Arg His His His His Cys
            20              25
```